United States Patent [19]

Posanski et al.

[11] Patent Number: 4,794,111
[45] Date of Patent: Dec. 27, 1988

[54] DIHYDROPYRIDINE PREPARATIONS CONTAINING β-BLOCKERS

[75] Inventors: Ulrich Posanski, Roesrath; Rainer Gross, Wuppertal; Stanislav Kazda, Wuppertal; Gerhard Schlüter, Wuppertal; Matthias Schramm, Cologne, all of Fed. Rep. of Germany

[73] Assignee: Bayer Aktiengesellschaft, Leverkusen, Fed. Rep. of Germany

[21] Appl. No.: 909,137

[22] Filed: Sep. 19, 1986

Related U.S. Application Data

[63] Continuation-in-part of Ser. No. 730,974, May 6, 1985, abandoned, and a continuation-in-part of Ser. No. 757,051, Jul. 19, 1985, abandoned.

[30] Foreign Application Priority Data

May 23, 1984 [DE] Fed. Rep. of Germany ....... 3419131
Jul. 25, 1984 [DE] Fed. Rep. of Germany ....... 3427402

[51] Int. Cl.⁴ ............... A61K 31/18; A61K 31/44; A61K 31/165; A61K 31/535
[52] U.S. Cl. .................. 514/236.2; 514/338; 514/344; 514/356; 514/605; 514/620; 514/652
[58] Field of Search ............. 514/356, 344, 352, 338, 514/229, 605, 620, 652

[56] References Cited

U.S. PATENT DOCUMENTS

| | | | |
|---|---|---|---|
| 3,619,370 | 11/1971 | Weinstock et al. | 195/51 |
| 3,655,663 | 4/1972 | Wasson | 544/134 |
| 3,657,237 | 4/1972 | Weinstock et al. | 544/134 |
| 3,663,607 | 5/1972 | Barrett et al. | 260/501.17 |
| 3,836,671 | 9/1974 | Barrett et al. | 514/620 |
| 3,935,267 | 1/1976 | Hauck et al. | 260/570.7 |
| 4,607,041 | 8/1986 | Baxter et al. | 514/340 |

FOREIGN PATENT DOCUMENTS

| | | |
|---|---|---|
| 3142853 | 5/1983 | Fed. Rep. of Germany ...... 514/356 |
| 1358951 | 7/1974 | United Kingdom . |
| 1516793 | 7/1978 | United Kingdom . |
| 2050375 | 1/1981 | United Kingdom . |
| 2037766 | 7/1986 | United Kingdom . |

OTHER PUBLICATIONS

Baldwin et al., J. Med. Chem., 1981 24, 628–631.
Esper et al., C. A. vol. 94 (1981) 94:168020w.
Abstracts, vol. 66, Supp. II, Oct. 1982, p. 120.
J. Med. Chem., Uloth et al., vol. 9, 1966, pp. 88–97.
S. H. Yalkowskay, Drugs and the Pharmaceutical Science, 12, 135–180, (1981) and J. Polderman, Formulation and Preparation of Dosage Forms, Elsevier/North Holland Biomedical Press, 1977, 215–219.
V. S. Wayne et al., in Australia N. Z. J. Med. 12, No. 4, 285–289, 1982.
M. D. Winniford et al. (Zirkulation 66, No. 4 Part 2, p. 1120 (1982) Dallas, U.S.A.
H. F. Brown, "Electrophysiology of the Sinoatrial Node", Physiol. Review, vol. 62, No. 2 (Apr. 1982), pp. 505–630.

*Primary Examiner*—Allen J. Robinson
*Attorney, Agent, or Firm*—Sprung Horn Kramer & Woods

[57] ABSTRACT

An antihypertensive and antianginal combination comprising (A) 0.1 to 10 parts by weight of an asymmetrical dihydropyridine of the formula

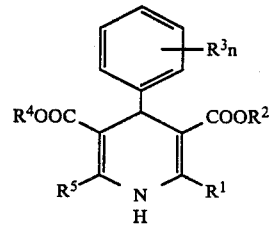

in which
$R^1$ and $R^5$ each independently is methyl, hydroxymethyl or cyano,
$R^2$ and $R^4$ are always different from one another and each independently is alkyl with 1 to 10 carbon atoms optionally substituted by alkoxy with 1 to 4 carbon atoms, fluorine, chlorine or N-methyl-benzylamino,
$R^3$ is nitro, chlorine, trifluoromethyl, or =N—O—N=, and n is 1 or 2,
and (B) about 10 to 200 parts by weight of a β-blocker preferably without a local anesthetic action.

7 Claims, No Drawings

DIHYDROPYRIDINE PREPARATIONS CONTAINING β-BLOCKERS

This application is a continuation-in-part of application Ser. No. 730,974, filed May 6, 1985, now abandoned, and application Ser. No. 757,051, filed July 19, 1985, now abandoned.

The invention relates to new dihydropyridine combination preparations in the solid form, having improved bioavailability, containing sparingly soluble dihydropyridines and β-blockers, to process for their preparation and to their use as medicaments, in particular as coronary and blood-pressure agents.

It has already been disclosed that dihydropyridines have very potent effects on the circulation (see British Pat. No. 1,358,951). Because of the sparing solubility of many dihydropyridines, a number of difficulties arise in the pharmaceutical preparation of medicinal specialities, as is evident from numerous publications and patent applications for special formulations of these active compounds. For example, British Pat. No. 1,456,618 describes and claims solid medicinal preparations which are likewise said to ensure good bioavailability of sparingly soluble dihydropyridines. Moreover, DT-OS (German published specification) No. 2,822,882 describes solid dosage forms in which the sparing solubility of the active compounds is said to be compensated for by the use of certain solubilizers and surface-active substances. In addition, the absorbability of dihydropyridines is said, in European Offenlegungsschrift (European published specification) No. 1,247 to be improved by the use of polyethylene glycol and certain porous carriers.

Likewise, various methods to improve the bioavailability, which is directly connected with improved solubility, are described in the literature. Apart from a change in the chemical structure, for example by incorporation of substituent groups which improve the solubility, a large number of methods which relate to a change in the physical properties of the active compounds has been described. Thus, for example, reduction in size of the particles of active compound, a change in the crystal structure, the preparation of salt forms, addition of wetting agents, complexation with other substances, use of biological carriers, production of solid dispersions (coprecipitates) or the preparation of surface adsorbates has been proposed (see S. H. Yalkowskay, Drugs and the pharmaceutical science, 12, 135–180 (1981) and J. Polderman, Formulation and preparation of dosage forms, Elsevier/North Holland Biomedical Press, 1977, 215–219).

All attempts to date to compensate for the poor solubility of dihydropyridines by particular measures and, at the same time, to ensure good bioavailability have a number of disadvantages. The use of surface-active subtances, solubilizers and certain carriers which have a particular surface, for example are porous, frequently leads to administration forms in which the preparations are undesirably large. To facilitate swallowing, tablets or capsules of this type are frequently converted into specific shapes such as, for example, ellipsoids or oblong shapes, but this still does not always lead to satisfactory results with preparations weighing more than 400 mg. Nor does the more frequent taking of smaller preparations represent a satisfactory solution.

A point about drug formulations is that both the number and the amount of the auxiliaries and vehicles should be kept as low as possible. When comparing two drug specialities, preference will always be given to that drug preparation which contains, in addition to the active compound, as few auxiliaries and additives as possible, in order essentially to avoid undesired biological side effects.

It is already known that combinations of various β-blockers with various calcium antagonists can be used in the treatment of circulatory diseases, in particular hypertension and coronary diseases. However, from the action mechanisms of calcium antagonists and of β-blockers, a higher risk in comparison with monotherapy can be deduced in respect of possible undesirable side effects. For example, V. S. Wayne et al., in Australia N.Z.J. Med. 12, No. 4,285–289 (1982), report serious side effects of a combination of the calcium antagonist verapamil and the β-blockers metoprolol and pindolol. M. D. Winniford et al. (Zirkulation 66, No. 4 Part 2, page 120 (1982) Dallas, U.S.A.) also report possible serious side effects in connection with the treatment of 13 angina patients with a combination of the β-blocker propanolol and the calcium antagonist verapamil. In contrast, the calcium antagonists selected according to the invention from the 1,4-dihydropyridine group are distinguished by a clearly better tolerance in this respect; if suitable β-blockers are chosen as combination partners, the benefit/risk ratio is further optimized.

The present invention relates to new solid combination preparations having improved bioavailability, containing 1 part by weight of a sparingly soluble dihydropyridine of the general formula (I)

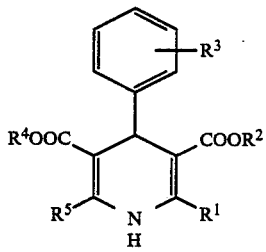

in which
R$^1$ and R$^5$ are identical or different and represent methyl, hydroxymethyl or cyano,
R$^2$ and R$^4$ represent alkyl with 1 to 10 carbon atoms, which is optionally substituted by alkoxy with 1 to 4 carbon atoms, fluorine, chlorine, N-methyl-benzylamino or trifluoromethyl benzylamino, and
R$^3$ represents 1 or 2 identical or different substituents from the group comprising nitro, chlorine and trifluoromethyl, or represents the radical =N—O—N=, and 0.5 to 10 parts by weight of a β-blocker, and, where appropriate, additional customary auxiliaries and vehicles.

Particular interest attaches to combination preparations according to the invention which contain a β-blocker from the group comprising acebutolol, prepranolol and pindolol, and preferably atenolol, nadolol, sotalol or timolol.

Particular interest attaches to combination preparations according to the invention which contain 1 part by weight of a dihydropyridine of the general formula I, in which R$^2$ and R$^4$ are different from one another, in particular nisoldipine, nimodipine or nitrendipine, and 1 to 10 and preferably 2 to 6 parts by weight of a β-blocker. Acebutolol and atenolol may be mentioned as preferred β-blockers.

In accordance with a further feature of the invention the β-blocker is one without a local anesthetic action and is present in 10 to 200 parts by weight per 0.1 to 10 parts by weight of the dihydropyridine.

The β-blockers which can be used according to the invention and have no local anaesthetic action are known (compare Uloth et al., J. Med. Chem. 9, 88 (1966), and U.S. Pat. Nos. 3,663,607, 3,836,671, 3,619,370, 3,655,663, 3,657,237 and 3,935,267).

Their use as combination partners with the unsymmetric dihydropyridines mentioned is new.

The β-blockers mentioned according to the invention are selected from the large group of known β-blockers. In the prior art, there are numerous indications that combinations of β-blockers with many calcium antagonists have the risk of undesirable side effects and can thus be used to only a limited degree for therapy of coronary and circulatory diseases. Knowledge of the mechanisms of the automaticity in cardiac pacemaker tissue and of the influences of calcium antagonists and β-blockers on these shows that, for example in animals treated with β-blockers, the spontaneous excitation of the cardiac pacemaker tissue may be lost if relatively high doses of calcium antagonists are simultaneously administered.

It could not be predicted that a combination of selected β-blockers without a local anaesthetic or sodium antagonistic action with the calcium antagonists selected according to the invention from the 1,4-dihydropyridine group shows such an advantageous action and is particularly distinguished by a good tolerance.

It is therefore decidedly surprising that the combinations according to the invention of selected calcium antagonists with selected β-blockers without a local anaesthetic (sodium antagonistic) action have a considerably better tolerance, coupled with an advantageous antihypertensive and antianginal action, than combinations with other β-blockers which have a local anaesthetic or sodium antagonistic action.

This applies all the more so since all the known electrophysiological investigations suggest that the sodium system plays no part in the automaticity of the pacemaker cells in the heart (compare, for example, Brown, H. F., Physiol. Rev. 62: 505–530 (1982)).

In the combination according to the invention, 1 part by weight of the dihydropyridine is advantageously brought together with 1 to 10, in particular 2 to 6, parts by weight of β-blocker. The daily dose of the combination according to the invention advantageously contains 1 to 100 mg, preferably 2 to 50 mg and in particular 5 to 30 mg, of dihydropyridine and 1 to 200 mg, preferably 10 to 100 mg and in particular 30 to 80 mg, of β-blocker.

The combination product according to the invention is preferably used as a solid formulation, for example in the form of tablets, pills, dragees, granules, powders, capsules or sachets.

The galenical formulations can be prepared in a known manner using known auxiliaries and excipients and, if appropriate, with the addition of other suitable active compounds, such as saluretics, in particular the active compounds mefruside or muzolimine.

Those combination products in which the active compound of dihydropyridine is employed in a sustained release formulation, such as, for example, in the form of active compound crystals with a specific surface area of 0.5 to 4 $m^2/g$, are to be particularly singled out. Another possibility for dihydropyridine is the use of a dihydropyridine which is in crystalline form to the extent of 60 to 100% and in amorphous form to the extent of 0 to 40%, for example as a co-precipitate with polyvinylpyrrolidone (PVP), methylcellulose, hydroxypropylcellulose or hydroxypropylmethylcellulose.

By using a mixture of amorphous dihydropyridine and crystalline dihydropyridine, the advantage of a rapid onset of action is combined with the advantage of a long duration of action.

The combination according to the invention is very well tolerated. Rats which had been beta-blocked by pretreatment with propranolol show the occurence of ECG-abnormalities (loss of artrial excitation) after intravenous infusion of a cummulative dose of nitrendipine of 2,5 mg/kg (infusion rate: 300 μg/kg/min). Rats which have been beta-blocked by pretreatment with sotalol tolerate a five-times higher dose of nitrendipine which is 12,2 mg/kg. If the rats were beta-blocked by pretreatment with atenolol a dosis of 6,8 mg/kg of nitrendipine was tolerated.

Besides the unexpectedly good tolerance of the combination according to the invention, which leads to a clear reduction in risk to the patient to be treated, the administration of the fixed combination according to the invention facilitates handling by the patient (improved patient compliance).

Other advantages of the combination according to the invention are to be seen in the fact that, in the case of serious circulatory diseases, in particular severe hypertension or coronary heart disease, when therapy with monoproducts is no longer successful, the combination product according to the invention can be conveniently and reliably used. Even if the handling ability of the patient is limited, intake of both active compounds in the combined form in the correct dosage is ensured and can be controlled more easily by the treating physician.

The combination preparations according to the invention are prepared by granulating the dihydropyridine active compound and the β-blocker active compound together with known auxiliaries using a moist granulation process or a dry compaction process and, where appropriate with at least one tabletting auxiliary, compressing the resulting granules to form tablets.

Examples of auxiliaries which may be mentioned are: disintegration promoters, such as starch, modified starch, cellulose, cellulose derivatives, crosslinked polyvinylpyrolidone (PVPP), sodium alginate and colloidal silica; binders, such as gelatine, tragacanth, glucose syrup, starch paste, polyvinylpyrrolidones (PVP), cellulose derivatives, polyethylene glycol MW 1000–5000 (PEG), and alginates; lubricants, such as magnesium stearate, calcium stearate, stearic acid, paraffin, talc, vegetable or animal fats, oils and waxes, polyethylene glycol MW 1000–5000 and silicones.

Examples of fillers which may be mentioned are: calcium sulphate, calcium carbonate, dibasic and tribasic calcium phosphates, magnesium carbonate, magnesium hydroxycarbonate, sodium chloride, sodium and potassium citrates, tartrates and succinates, starch, modified starch, cellulose, powdered cellulose, sugars, such as lactose, sucrose or dextrose, and sugar alcohols, such as mannitol or sorbitol.

Particular interest attaches to auxiliaries and fillers from the group comprising starch, modified starch, such as starch paste, cellulose, PVP, PVPP, colloidal silica, lactose, magnesium carbonate, magnesium stearate and calcium stearate.

It is surprising, from a knowledge of the state of the art, that it is possible to achieve a significant increase in the release, and thus a significant improvement in the bioavailability, of a sparingly soluble dihydropyridine by granulation of the dihydropyridine together with one of the β-blockers mentioned. This effect does not depend on the presence of additional auxiliaries which, according to knowledge according to the state of the art, increase the rate of release, such as, for example, complexing agents, surface-active substances or water-soluble polymers.

Sparingly soluble dihydropyridines which may be mentioned are dihydropyridines whose solubility is not more than 20 mg per liter of water at 25° C.

In a release test using the USP paddle method under the following conditions:
4,000 ml of 0.1N hydrochloric acid
paddle rotating at 100 rpm,
rates of release of nitrendipine of about 80% after 2 hours were reached with combination preparation according to the invention (product of Example 1). A corresponding formulation of a conventional nitrendipine tablet, in which the nitrendipine used was in the same crystalline composition and which contains the same auxiliaries, shows a rate of release of only about 40% after 2 hours. The progress of the release is evident from Table 1.

TABLE 1

In vitro release from tablets containing nitrendipine (USP paddle method)

| Release time [h] | Cumulative release of nitrendipine as a percentage of the dose used | |
|---|---|---|
| | Tablet Example 1 | Tablet Comparison Example |
| 0.25 | 24 | 8 |
| 0.5 | 52 | 19 |
| 1 | 68 | 36 |
| 2 | 82 | 43 |

COMPARISON EXAMPLE 100 g of nitrendipine, 910 g of corn starch, 680 g of powdered cellulose and 550 g of calcium carbonate and 10 g of sodium lauryl sulphate are mixed for 5 minutes in a planetary mixer, and granulated with an aqueous solution of polyvinylpyrrolidone (solids content 50 g) for 10 minutes. The moist composition is passed through a screen and dried in a fluidized bed drier to a final water content of about 4.5%. The dried granules are made uniform by screening (0.8 mm mesh size of screen) and vigorously mixed with 50 g of magnesium stearate. The granules are then compressed to form tablets weighing 235 mg.

EXEMPLARY EMBODIMENTS

Example 1

100 g of nitrendipine, 500 g of atenolol, 660 g of corn starch, 430 g of powdered cellulose, 550 g of calcium carbonate and 10 g of sodium lauryl sulphate are mixed in a planetary mixer for 5 minutes and granulated with an aqueous solution of polyvinylpyrrolidone (solids content 50 g) for 10 minutes. The moist composition is passed through a screen and dried in a fluidized bed drier to a final water content of about 4.5%. The dried granules are made uniform by screening (0.8 mm mesh size of screen) and vigorously mixed with 50 g of magnesium stearate. The granules are then compressed to form tablets weighing 235 mg. The tablets can be coated with a protective lacquer.

Example 2

50 g of nisoldipine, 2,216 g of acebutolol hydrochloride, 2,244 g of corn starch, 250 g of corn starch which has been converted to a paste beforehand, and 750 g of powdered cellulose are granulated in a mixing granulator with an aqueous solution of Tween 80 (content 15 g). The moist composition is then passed through a rasp (perforation size 4.0 mm) and dried to a residual moisture content of about 3.8% in a circulating air drying oven. The dried granules are made uniform by screening (1.25 mm mesh size of screen) and vigorously mixed with 15 g of magnesium stearate. The granules are then compressed to form tablets weighing 277 mg.

Example 3

20 mg of nitrendipine, consisting of 15 mg of microcrystalline active compound with a specific crystal surface area of about 3 $m^2/g$ and 5 mg of nitrendipine co-precipitate with PVP, are mixed together with 50 mg of crystalline atenolol, 370 mg of microcrystalline cellulose, 85 mg of lactose and 7 mg of magnesium stearate and the mixture is pressed to tablets.

Example 4

20 mg of nitrendipine, consisting of 5 mg of microcrystalline active compound with a specific crystal surface area of about 3 $m^2/g$ and 15 mg of nitrendipine co-precipitate with PVP, are mixed together with 25 mg of crystalline atenolol, 150 mg of microcrystalline cellulose, 110 mg of corn starch, 30 mg of crospovidone and 5 mg of magnesium stearate and the mixture is pressed to tablets.

Example 5

30 mg of nitrendipine, consisting of 10 mg of microcrystalline active compound with a specific crystal surface area of about 3 $m^2/g$ and 20 mg of nitrendipine co-precipitate with PVP, are mixed with 60 mg of crystalline timolol, 200 mg of microcrystalline cellulose, 150 mg of corn starch, 35 mg of crospovidone and 5 mg of magnesium stearate and the mixture is pressed to tablets.

Example 6

(Only for nitrendipine)

50 mg of nitrendipine as a microcrystalline active compound with a specific crystal surface area of about 3.5 $m^2/g$ are mixed with 100 mg of crystalline timolol, 50 mg of microcrystalline cellulose, 70 mg of corn starch, 26 mg of lactose, 20 mg of PVP, 2 mg of sodium lauryl-sulphate and 2 mg of magnesium stearate and the mixture is pressed to tablets.

Example 7

10 mg of nitrendipine as a microcrystalline active compound with a specific crystal surface area of about 3 $m^2/g$ are mixed with 50 mg of crystalline sotalol, 27.5 mg of corn starch, 20 mg of microcrystalline cellulose, 16 mg of calcium hydrogen phosphate, 5 mg of PVP, 1 mg of polysorbate and 0.5 mg of magnesium stearate and the mixture is pressed to tablets.

Example 8

20 mg of nitrendipine as a microcrystalline active compound with a specific crystal surface area of about 3 m$^2$/g are mixed with 30 mg of crystalline nadolol, 28.5 mg of corn starch, 25 mg of microcrystalline cellulose, 20 mg of magnesium carbonate, 5 mg of PVP, 1 mg of sodium lauryl-sulphate and 0.5 mg of magnesium stearate and the mixture is pressed to tablets.

Example 9

20 mg of nisoldipine as a microcrystalline active compound with a specific crystal surface area of about 2.5 m$^2$/g are mixed with 120 mg of crystalline atenolol, 80 mg of microcrystalline cellulose, 66 mg of corn starch, 40 mg of lactose, 10 mg of PVP, 2 mg of sodium lauryl-sulphate and 2 mg of magnesium stearate and the mixture is pressed to tablets.

Example 10

10 mg of nitrendipine as a microcrystalline active compound with a specific crystal surface area of about 2.5 m$^2$/g are mixed with 60 mg of crystalline sotalol, 40 mg of microcrystalline cellulose, 33 mg of corn starch, 20 mg of lactose, 5 mg of PVP, 1 mg of sodium lauryl-sulphate and 1 mg of magnesium stearate and the mixture is pressed to tablets.

Example 11

5 mg of nitrendipine as a microcrystalline active compound with a specific crystal surface area of about 3 m$^2$/g are mixed with 40 mg of crystalline nadolol, 30 mg of microcrystalline cellulose, 29 mg of corn starch, 20 mg of magnesium carbonate, 5 mg of PVP, 0.5 mg of polysorbate and 0.5 mg of magnesium stearate and the mixture is pressed to tablets.

Example 12

1 mg of nitrendipine as a microcrystalline active compound with a specific crystal surface area of about 2.5 m$^2$/g are mixed with 70 mg of crystalline timolol, 20 mg of microcrystalline cellulose, 15 mg of calcium hydrogen phosphate, 8 mg of corn starch, 0.5 mg of sodium lauryl-sulphate and 0.5 mg of magnesium stearate and the mixture is pressed to tablets.

Example 13

(Only for nisoldipine)

0.5 mg of nisoldipine as a microcrystalline active compound with a specific crystal surface area of about 3.5 m$^2$/g are mixed with 25 mg of crystalline atenolol, 20 mg of cellulose powder, 10 mg of lactose, 19.7 mg of corn starch, 4 mg of PVP, 0.5 mg of sodium lauryl-sulphate and 0.3 mg of magnesium stearate and the mixture is pressed to tablets.

It will be understood that the specification and examples are illustrative but not limitative of the present invention and that other embodiments within the spirit and scope of the invention will suggest themselves to those skilled in the art.

What is claimed is:

1. A composition comprising by weight a synergistically effective mixture of
   (A) 0.1 to 10 parts of a dihydropyridine selected from the group consisting of nisoldipine, nimodipine and nitrendipine
   (B) about 10 to 200 parts of a β-blocker selected from the group consisting of atenolol, sotalol, timolol and nadolol which is without local anesthetic action.

2. A composition according to claim 1, wherein (A) is selected from the group consisting of nitrendipine and nisoldipine.

3. A composition according to claim 1, wherein (A) and (B) are present in a weight ratio of 1:2–6.

4. A unit dose of a composition according to claim 1, in the form of a tablet, capsule or ampule containing 1 to 100 mg of (A) and 1 to 200 mg of (B).

5. A unit dose of a composition according to claim 1, in the form of a tablet, capsule or ampule containing 5 to 30 mg of (A) and 30 to 80 mg of (B).

6. A composition according to claim 1, in the form of granules.

7. A method of combating hypertension in a patient which comprises administering to a patient in need thereof an antihypertensive effective amount of the composition of claim 1.

* * * * *